(12) United States Patent
Fermigier et al.

(10) Patent No.: US 9,164,201 B2
(45) Date of Patent: Oct. 20, 2015

(54) LENS HAVING A PLURALITY OF SURFACES WITH ZONES

(75) Inventors: Bruno Fermigier, Charenton le Pont (FR); Eric Gacoin, Charenton le Pont (FR)

(73) Assignee: ESSILOR INTERNATIONAL (COMPAGNIE GENERALE D'OPTIQUE, Charenton le Pont (FR)

( * ) Notice: Subject to any disclaimer, the term of this patent is extended or adjusted under 35 U.S.C. 154(b) by 37 days.

(21) Appl. No.: 14/346,032

(22) PCT Filed: Sep. 6, 2012

(86) PCT No.: PCT/FR2012/051999
§ 371 (c)(1),
(2), (4) Date: Mar. 20, 2014

(87) PCT Pub. No.: WO2013/041791
PCT Pub. Date: Mar. 28, 2013

(65) Prior Publication Data
US 2014/0226221 A1    Aug. 14, 2014

(30) Foreign Application Priority Data
Sep. 20, 2011 (FR) ...................................... 11 58339

(51) Int. Cl.
G02B 3/08 (2006.01)
B29C 59/02 (2006.01)
G02C 7/02 (2006.01)
A61F 2/16 (2006.01)

(52) U.S. Cl.
CPC ................. G02B 3/08 (2013.01); B29C 59/022 (2013.01); G02C 7/02 (2013.01); *A61F 2/1656* (2013.01); *G02C 2202/16* (2013.01); *G02C 2202/20* (2013.01)

(58) Field of Classification Search
CPC .......... G02B 3/08; B29C 59/022; G02C 7/02; G02C 2202/16; G02C 2202/20; A61F 2/1656
See application file for complete search history.

(56) References Cited

U.S. PATENT DOCUMENTS

2002/0063862 A1    5/2002    Kitamura et al.

FOREIGN PATENT DOCUMENTS

| FR | 2 057 540 A5 | 5/1971 |
|---|---|---|
| GB | 1 154 360 A | 6/1969 |

(Continued)

OTHER PUBLICATIONS

NPL English-Language translation of International Preliminary Report on Patentability (Chapter I) prepared for PCT/FR2012/051999 on Mar. 25, 2014.*

(Continued)

*Primary Examiner* — David N Spector
(74) *Attorney, Agent, or Firm* — Young & Thompson (57) ABSTRACT

A lens (1) includes a plurality of optical surfaces ($S_1$, $S_2$) each of which is made up of an alternation of active zones ($ZA_1$, $ZA_2$) and separation zones ($ZS_1$, $ZS_2$). The active zones of one of the surfaces are situated beside the separation zones of the other surface. The shape of one at least of the optical surfaces is then adapted into the separation zones in order to augment the acute angles that are situated at the convergence of active zones and separation zones. The lens can thus be made with improved accuracy with respect to a target optical function.

14 Claims, 9 Drawing Sheets

(56) References Cited

FOREIGN PATENT DOCUMENTS

| | | |
|---|---|---|
| JP | 57 109618 A | 7/1982 |
| JP | 63 106737 A | 5/1988 |
| JP | 7 241919 A | 9/1995 |
| WO | 2011/079856 A1 | 7/2011 |

OTHER PUBLICATIONS

International Search Report, dated Dec. 20, 2012, from corresponding PCT application.

* cited by examiner

LENS HAVING A PLURALITY OF SURFACES WITH ZONES

The present invention relates to a lens comprising a plurality of zonal surfaces. It in particular relates to an improvement to Fresnel lenses that have already been proposed or used.

As is known, a Fresnel lens, which is a lens comprising one or more zonal surfaces and zonal jumps, may have an equivalent optical power to that of a smooth-surface lens, while having a smaller thickness. The thickness and weight reduction that result therefrom are advantageous for certain applications, among which ophthalmic applications.

A Fresnel lens comprises, on at least one of these optical surfaces, sagittal height jumps between adjacent zones inside this optical surface. Specifically, for a refractive Fresnel lens, the optical power is produced by the curvature of the optical surface inside each zone, in a way that is almost independent of a shift in the optical surface in this zone parallel to the optical axis of the lens. For this reason, in zones of the lens where its thickness would be too great, it is possible to shift the surface of the lens parallel to its optical axis in order to reduce the thickness thereof, thereby creating a sagittal height jump in the optical surface at the limit of the zone in question.

However, in order for such a Fresnel lens to possess sufficient optical quality, it is necessary for it to be possible for its optical surface, in each Fresnel zone, to be produced with precision in accordance with a target-surface, the latter possibly corresponding to the smooth-surface lens.

Figure 1:
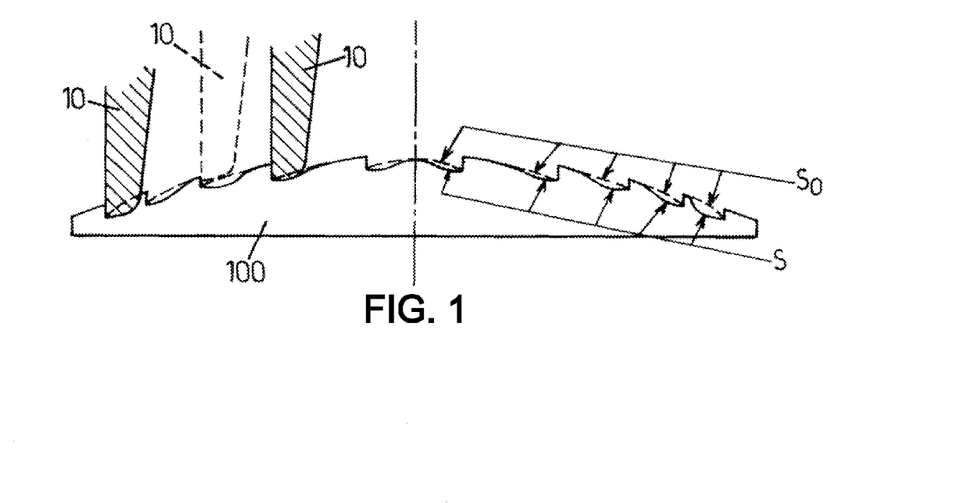
FIG. 1 illustrates a difficulty with machining a molding insert of a Fresnel lens, such as existed before the present invention.

Now, the zonal surface of a Fresnel lens that is made of polymer may be produced either by embossing using embossing matrices, or by molding using molding inserts, or by direct machining of a Fresnel-lens blank. For the first two processes, the embossing matrices and the molding inserts comprise master-surfaces that are complementary to the zonal surface that is sought for the lens. The optical quality of the Fresnel lens therefore depends on whether it is actually possible to machine each master-surface with precision in accordance with the target-surface. Most often, the embossing matrices and the molding inserts are made of metal, and machined by moving a subtractive tool over their surface. However, this tool possesses, at its working end, a profile that is defined to give it sufficient rigidity and robustness. In particular, the working end of the tool has a set tip angle and edge length, which determine the minimum size of patterns that can be machined. These tool dimensions especially prevent the target-surface from being obtained for a Fresnel-lens master-surface on a line of re-entrant angle between two adjacent zones. FIG. 1 illustrates such a problem, with the following references:

$S_O$: target-surface with Fresnel zones,
100: embossing matrix or molding insert,
10: subtractive machine tool, for three positions of this tool for producing sagittal height jumps; and
S: example surface actually obtained by machining.

FIG. 1 shows the surface S that is actually obtained if the tool 10 is advanced until it reaches the bottom of the re-entrant angles that are located at the base of the sagittal height jumps, an excess of material being removed with the back of the tool 10 that is opposite its angle of attack. In contrast, the advance of the tool 10 may be decreased in order not to exceed the target-surface $S_O$, but in this case the height jumps are shortened (see the position of the tool 10 that is indicated by dotted lines).

Even if, during embossing or molding, the polymer that forms the Fresnel lens then exactly adopts the shape of the master-surface, the optical quality of the resulting lens is limited by the machining deviation between the master-surface and the target-surface.

This limitation also arises, in a similar way, for a Fresnel lens the zonal surface of which is machined directly.

Furthermore, the same difficulties arise for the production of a diffractive lens that also possesses a zonal surface, with sagittal height jumps between two adjacent zones.

One aim of the present invention is thus to provide lenses the optical surfaces of which are divided into zones with intermediate sagittal height jumps, and which have improved optical qualities. In particular, the aim of the invention is to reduce forming and machining defects for such zonal-surface lenses.

To do this, the invention provides a lens that comprises at least two optical surfaces each of which extend transversely relative to an optical axis of the lens, so that light rays that pass through the lens pass through one then the other of the two surfaces, each surface comprising active zones inside of which a shape of this surface is adapted to produce part at least of the optical power of the lens for rays that pass through these active zones, with a sagittal height discontinuity of each surface between two different active zones of this surface. Furthermore, limits of the active zones of a first of the two surfaces are located in line with limits of the active zones of the other of the two surfaces, along the optical axis of the lens.

In the context of the invention, the expression "in line with" is used without distinction of meaning with "facing", especially in the case where the invention is applied to a lens that has a cambered base. The alignment that is thus designated by the expressions "in line with" or "facing" refers to the direction of propagation of light rays between the two optical surfaces of the lens, for a use of the latter. Specifically, the present invention applies to an optical component that may either have:

a planar base: for each surface of the lens, the tips or bottoms of the sagittal height jumps are located in the same planar perpendicular to the optical axis. In this first case, the limits of the active zones of the first of the two surfaces may be located in line with the limits of the active zones of the other of the two surfaces along the optical axis of the lens; or a cambered base: for each surface of the lens, the tips or bottoms of the sagittal height jumps are located on a sphere or an aspheric surface that is parallel to a given reference surface, called the base. In this second case, the zones of the two surfaces may be said to be facing when they are aligned along a direction that is perpendicular to the base.

In fact, these two cases are equivalent relative to the shape of the base of the lens.

Moreover, in each planar- or cambered-base case, the sagittal height jumps each have a jump direction that may be parallel to the optical axis of the lens or inclined relative to this axis. When the jump direction is inclined relative to the optical axis, the limits between the active zones of the first surface may be located in line with—or facing—those of the other surface, preferably, along this jump direction.

The lens of the invention is characterized in that the first and second surfaces furthermore comprise separating zones that are arranged so that each surface consists of an alternation between active zones and separating zones. In addition, each active zone of one of the first and second surfaces is in line with—or facing—a separating zone of the other surface. In other words, the two surfaces are partitioned in a complementary way into active zones and separating zones. According to this partition, the active zones may contribute to the optical power of the lens in a measure superior to that of the separating zones.

According to an additional feature of the lens of the invention, the shape of at least one of the first and second surfaces in at least one of the separating zones is adapted to increase at least one of the following angles:
- a first angle that is formed by this surface in the separating zone with a direction of a sagittal height jump located at the limit between this separating zone and an active zone that is adjacent to the latter,
- a second angle that is formed by this surface at the limit between the separating zone and an active zone that is adjacent to the latter, and
- a third angle that is formed by the other surface at the limit of the active zone of this other surface that is located in line with the separating zone in question, this third angle being formed by the other surface in the active zone with a direction of a sagittal height jump located at the limit of this active zone.

Each of these angular increases is considered relative to an angle that is located a given location of the lens and formed by an imaginary surface obtained by subtracting respective sagittal heights of the two surfaces, this angle for the imaginary surface being acute. Most often, the imaginary surface that is obtained by subtracting sagittal heights of the real optical surfaces is a conventional Fresnel lens, i.e. such as was known before the present invention.

These angular increases allow a subtractive machine tool, which is used to produce the optical surfaces of the lens, to reach the tip of the angles of the surfaces that are located in the location of sagittal height jumps.

In addition, one or both optical surfaces in its (their) separating zones may (may) have shapes that are designed to reciprocally compensate for machining divergences, which exist in the active zones, between the shapes of the surfaces that are actually obtained and the corresponding shapes that are sought.

In this way, the distribution of the optical power of the lens between two optical surfaces that are separate, with complementary partitions of each of these surfaces into active zones and separating zones, allows the optical quality of the lens that is produced to be improved.

According to one improvement of the invention, for at least one of the first and second surfaces of this lens, the surface may have a shape, on at least one side of a sagittal height jump of this surface, at the limit between a separating zone and an active zone, that is adapted to compensate a forming defect at the tip of an angle of the other surface, which angle is located in line with the limit of the zone in question. Optionally, such an adaptation of the shape of the surface may be implemented on both sides of the sagittal height jump. The optical surfaces may thus be produced with an improved exactitude, relative to the target-surface.

In various embodiments of the invention, one or more of the following improvements may advantageously be applied, each alone or a number in combination:
- a sagittal height variation amplitude of each of the first and second surfaces, or deviation of this surface relative to the base, in at least one of the separating zones of this surface may be smaller than 25% of a sagittal height variation amplitude of the other surface in the active zone that is located in line with the separating zone in question;
- each of the first and second surfaces may be planar or, more generally, correspond to the planar or cambered base of the lens, inside each separating zone;
- the active zones and the separating zones may be concentric inside each of the first and second surfaces; and
- for at least one of the limits between an adjacent active zone and separating zone of one of the optical surfaces, a sagittal height jump direction at this limit may be coincident with a direction of alignment of the same limit with a limit between adjacent separating and active zones of the other optical surface;

the part of the optical power of the lens that is produced by the first and second surfaces results from a refraction or a diffraction of light in the active zones and the separating zones of each surface. In other words, the lens of the invention may be a lens of the Fresnel or diffractive lens type.

The invention may advantageously be applied to the ophthalmic field, for which the demand for optical quality is high. In this case, the lens is of the ophthalmic lens type, including therein spectacle glasses, contact lenses and ocular implants. Such an ophthalmic lens possesses additional specific characteristics, such as a base value that may be added to the curvatures of the optical surfaces.

According to a particular embodiment of the lens, the latter may comprise at least two lens parts that are separate, with a first of these lens parts forming the first optical surface and a second of these lens parts forming the second optical surface. These two lens parts are advantageously arranged so that the two optical surfaces are turned toward each other. Such an embodiment is advantageous because the two optical surfaces are mutually protected from attacks or dirt that originate from the external environment. According to one improvement to such an embodiment, the two lens parts may have patterns that are complementary in a peripheral zone of the lens, these patterns being adapted to produce an alignment of the two lens parts relative to each other during assembly of said parts to form the lens.

The invention also relates to an assembly for forming a lens, which comprises two master-surfaces adapted to form the first and second optical surfaces, respectively, of a lens according to the invention, such as described above. In particular, this forming assembly may consist of a pair of embossing matrices or a pair of molding inserts. These embossing matrices or molding inserts then respectively comprise the first and second master-surface.

Other features and advantages of the present invention will become apparent from the following description of nonlimiting example embodiments, given with reference to the appended drawings, in which:

FIG. 2b is a cross section of a set of molding inserts adapted to produce a Fresnel lens according to FIG. 2a;

For the sake of clarity, the dimensions of the elements that are shown in these figures do not correspond to their actual dimensions and the ratios of these dimensions are not the actual ratios. In addition, patterns having identical functions that exist repeatedly in a lens or a forming assembly are shown only a limited number of times, without relation to reality, in order to allow them to be enlarged in the figures. Lastly, identical references that feature in different figures denote identical elements or elements that have identical functions.

The invention is now described in detail in the context of the production of Fresnel lenses. As is known, the optical power and the possible astigmatism of such a lens result from the refraction of light rays at the two optical surfaces of the lens. However, it will be understood that the description may be transposed to the production of diffractive lenses, by making thereto modifications that are within the ability of those skilled in the art, no inventive step being required.

The invention is also described in the case of a monolithic lens for the sake of simplicity, but it will be indicated, at the end of the description, that the lens may be made up of a number of assembled parts, with optical surfaces to which the invention is applied, which surfaces are borne by separate lens parts.

Figure 2A:
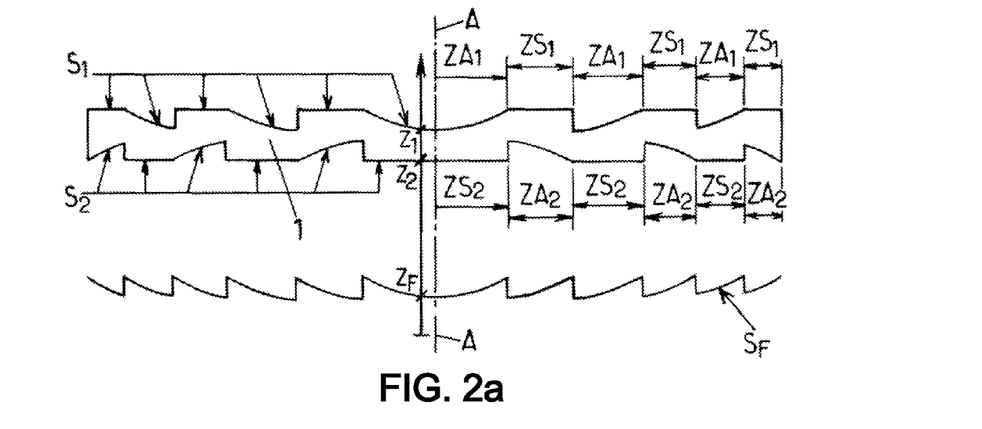
FIG. 2a is a cross section of a Fresnel lens illustrating a first aspect of the invention.

In FIG. 2a, a Fresnel lens 1 that is in accordance with the invention possesses at least two optical surfaces $S_1$ and $S_2$. These surfaces are shifted parallel to the optical axis A-A of the lens 1, so that they are passed through, one after the other, by the same light rays that form an image through the lens. For example, $S_1$ and $S_2$ may be the front optical surface and the back optical surface, respectively, of the lens 1, relative to the direction of propagation of the light rays.

As is known, each surface $S_1$, $S_2$ may be defined by sagittal height values that are defined at every point on this surface. Simply, the sagittal height of a point of each surface $S_1$, $S_2$ is the distance, measured parallel to the optical axis A-A, between this surface and a reference planar that is perpendicular to the axis A-A. In FIG. 2a, the axis, parallel to the optical axis A-A, used to measure the sagittal height is denoted z, and $z_1$ and $z_2$ are respective sagittal height values of the surfaces $S_1$ and $S_2$. The sagittal height $z_1$, $z_2$ of each surface $S_1$, $S_2$ then continuously varying inside zones in which this surface is itself continuous. In contrast, between two adjacent zones, each surface may have a discontinuity in sagittal height along an intermediate limit between these zones, with a sagittal height jump value that forms a measure of the discontinuity. Each surface may also be continuous along an intermediate limit between two zones, having instead a tangent planar rupture, or inclination discontinuity, along this limit.

According to a first feature of the invention, the two optical surfaces $S_1$ and $S_2$ are each partitioned with a common segmentation. When the zones of the segmentation of the two surfaces are concentric, machining of the lens or a forming element of the latter is simpler, and may be carried out with a lathe. Thus, the surface $S_1$ is divided into two families of zones that are alternated, respectively active zone that are designated by $ZA_1$ and separating zones that are designated by $ZS_1$. Likewise, the surface $S_2$ is simultaneously divided into active zones $ZA_2$ that are alternated with separating zones $ZS_2$. The limits between adjacent zones $ZA_1/ZS_1$ in the surface $S_1$ are aligned with the optical axis A-A, and with the limits between adjacent zones $ZA_2/ZS_2$ in the surface $S_2$. In this sense, the limits between the zones $ZA_1/ZS_1$ face the limits between the zones $ZA_2/ZS_2$. In addition, each active zone $ZA_1$ of the surface $S_1$ is located in line with, along the axis A-A, or facing, a separating zone $ZS_2$ of the surface $S_2$. Simultaneously, each separating zone $ZS_1$ is located in line with an active zone $ZA_2$.

As will be explained below, the active zones of the two optical surfaces produce most or even all of the optical power and possible astigmatism of the lens 1. To do this, each surface $S_1$, $S_2$ possesses appropriate curvature values in its active zones $ZA_1$, $ZA_2$. By way of example, the optical surfaces $S_1$ and $S_2$ that are shown in the figures correspond to divergent lenses, because these surfaces are concave for the lens in the active zones $ZA_1$ and $ZA_2$. The contribution, called the Fresnel contribution, of each optical surface $S_1$, $S_2$ in the corresponding separating zones $ZS_1$, $ZS_2$, to the optical power and to the possible astigmatism of the lens 1, is preferably either zero, or smaller than that of the active zones $ZA_1$, $ZA_2$. Specifically, this surface is coincident with the base, or close to this base, in the separating zones, whether the base is planar or cambered. In fact, as will be explained below, when they are not zero, the contributions of the surfaces $S_1$, $S_2$ in the separating zones $ZS_1$, $ZS_2$ may be reduced to a function for compensating defects in the contributions of the active zones $ZA_1$, $ZA_2$, relative to a target-surface of the lens 1 that corresponds to its values of optical power and astigmatism. When the contributions of the separating zones $ZS_1$, $ZS_2$ to the optical power and to the astigmatism of the lens are zero, the surfaces $S_1$ and $S_2$ may be planar or, more generally, coincident with the base inside these zones.

As is known, the expression "surface equivalent to a lens having two optical surfaces" is understood to mean the imaginary surface $S_F$ that is defined by subtracting its optical surfaces: $z_F = z_1 - z_2$, where $z_1$ is the sagittal height of the surface $S_1$, $z_2$ is the sagittal height of the surface $S_2$, and $z_F$ is the sagittal height of the imaginary surface $S_F$, the three sagittal heights $z_1$, $z_2$ and $z_F$ being considered, for the surface subtraction operation, at points that are aligned parallel to the optical axis A-A. In this surface subtraction operation, which is carried out point-by-point in a set direction, the negative sign corresponds to an algebraic orientation of the surfaces $S_1$ and $S_2$ relative to the direction of propagation of the light rays through the lens 1. At the bottom of FIG. 2a, the surface $S_F$ that is shown is the imaginary surface that is equivalent to the Fresnel lens 1 in the same figure.

The optical function of a lens is set by a target-surface that is adopted for the imaginary surface $S_F$ equivalent to the lens. However, a given target-surface may be produced in various ways by associating optical surfaces $S_1$ and $S_2$ that are able to reproduce the imaginary target-surface by being subtracted from each other. The feature of the invention that provides the separating zones $ZS_1$, $ZS_2$ of each surface $S_1$, $S_2$ with a compensation function relative to the active zones is based on this principle.

Figure 2B:
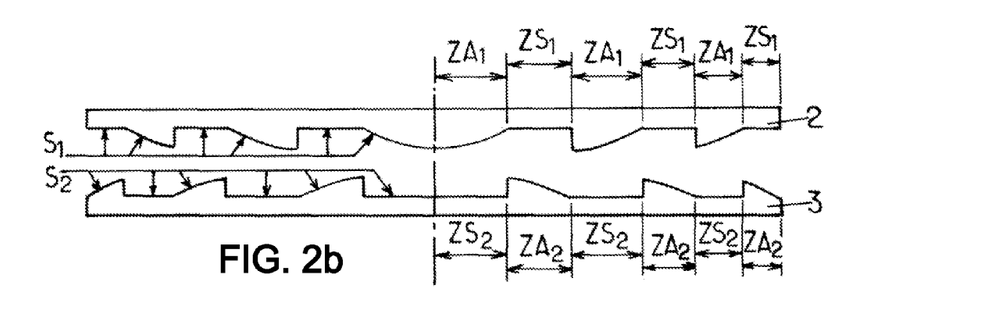

FIG. 2b shows a pair of molding inserts that is adapted to produce the lens 1 in FIG. 2a. The two inserts are designated by the references 2 and 3, respectively, and are intended to be placed facing inside a mold for injection molding the polymer of the lens 1. Therefore, the inserts 2 and 3 possess master-surfaces that correspond to the surfaces $S_1$ and $S_2$ of the lens 1 to be produced. For this reason, the surfaces $S_1$ and $S_2$ are shown in FIG. 2b, with the zones $ZA_1$, $ZS_1$, $ZA_2$ and $ZS_2$. The present description is first given for the particular case of molding inserts, but it will be understood that it may be directly transposed to embossing matrices.

Figure 3A:
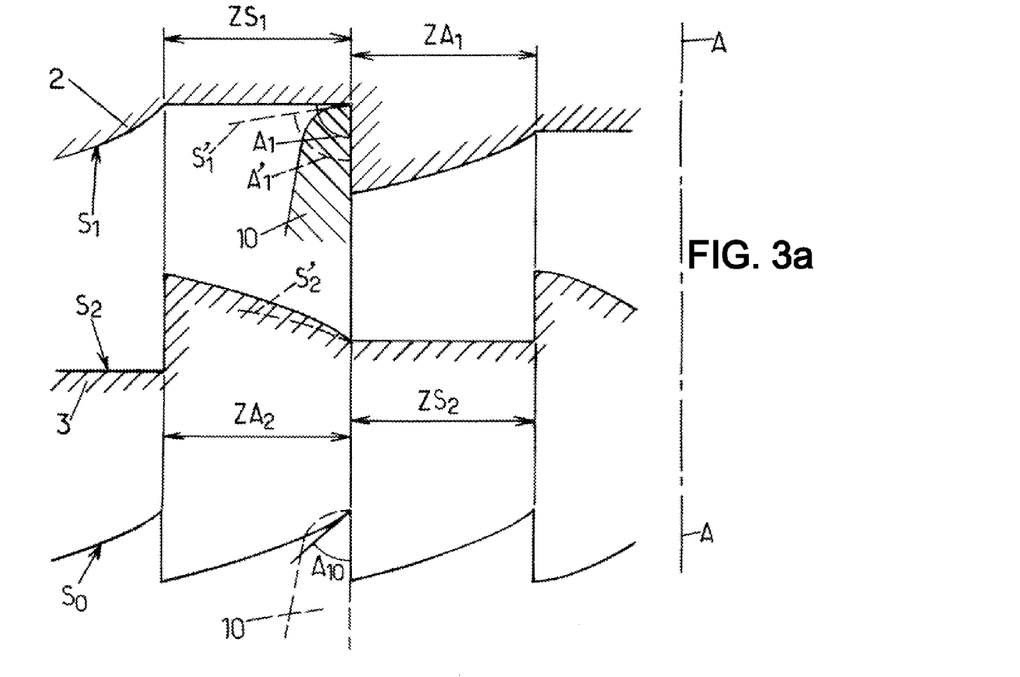
FIG. 3a is a cross-section of molding inserts according to a first implementation of the invention.
Figure 3B:
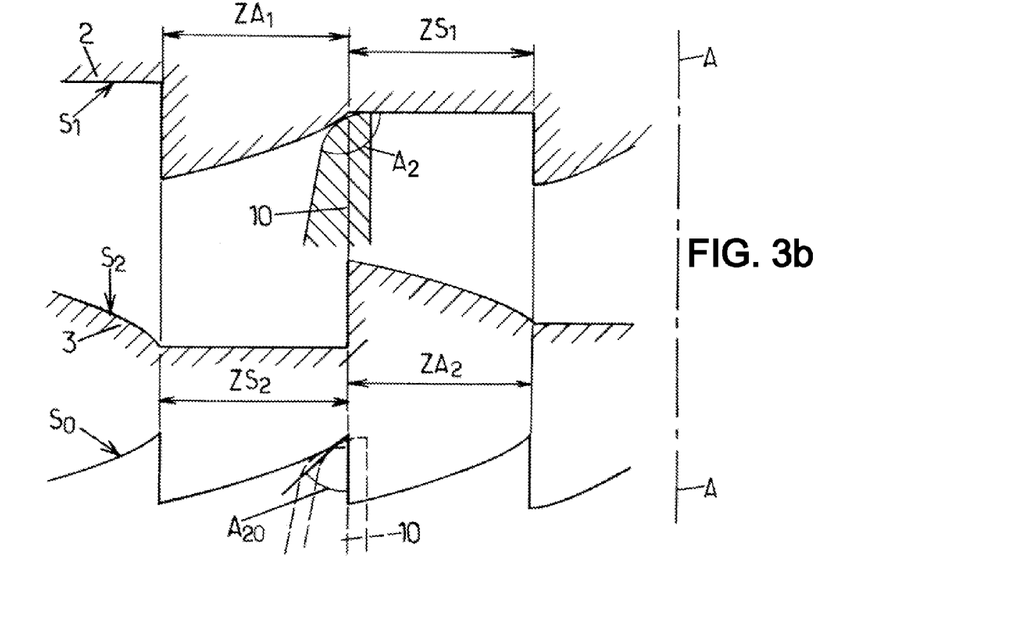
FIGS. 3b and 3c correspond to FIG. 3a for two other implementations of the invention.
Figure 3C:
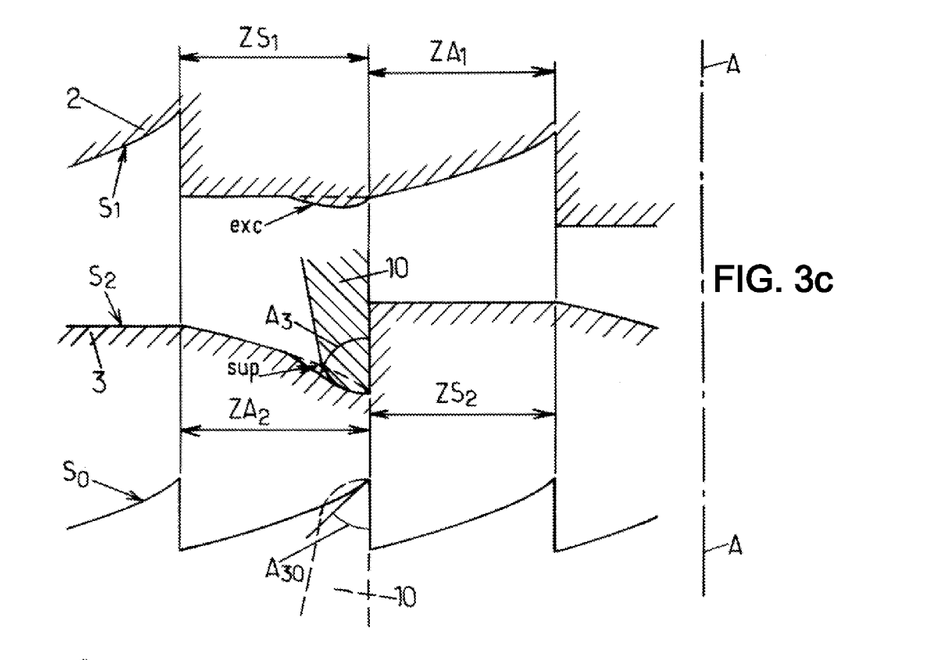

FIGS. 3a-3c, which are now described in succession, correspond to three separate implementations of the invention for the molding inserts 2 and 3. Each of these figures is an enlarged view of the surfaces $S_1$ and $S_2$, their alignment along the axis A-A being used again. It also shows the corresponding target-surface $S_0$, in order to allow the improvement provided by the invention to be seen. The direction of the sagittal height jumps is again the optical axis A-A.

These figures show modifications to the angles formed by one or other of the surfaces $S_1$ and $S_2$, which are obtained by virtue of the modification of the surface $S_1$ in a separating zone $ZS_1$ according to the invention. However, it will be understood that an identical advantage may be obtained by applying the invention to the surface $S_2$. Furthermore, the embodiments that are shown may be combined together, to obtain combinations of their respective advantages.

The reference 10 designates the subtractive machine tool that is used to produce the inserts 2 and 3 using a lathe. A position of this machine tool is indicated in each of FIGS. 3a-3c, which position is allowed by the invention on one or other of the surfaces $S_1$ or $S_2$, and the corresponding tool position of which would not possible for the target-surface $S_0$ if the latter were adopted to form a single lens optical surface.

The implementation of the invention that is illustrated in FIG. 3a is the simplest. It relates to placing the machine tool 10 to form the bottom of a sagittal height jump, when the insert surface $S_1$ is recessed in the separating zone $ZS_1$ relative to the adjacent active zone $ZA_1$. Initially, it is assumed that each of the surfaces $S_1$, $S_2$ is planar in the corresponding separating zones. The surface $S_1$ therefore forms an angle $A_1$ that is equal to 90° between this surface in the separating zone $ZS_1$ and the direction of the sagittal height jump that separates this zone $ZS_1$ from the adjacent active zone $ZA_1$. As regards the corresponding angle $A_{10}$ on the target-surface $S_0$, it is smaller than 90° because of the inclination of the surface $S_2$ in the active zone $ZA_2$ that is in line with the zone $ZS_1$. The introduction of the tool 10 as far as the tip of the angle $A_1$ is possible on the surface $S_1$, whereas it would not be possible to introduce the same tool 10 as far as the tip of the angle $A_{10}$ on the target-surface $S_0$ (see the tool position indicated by the dotted lines).

The two dotted lines $S'_1$ and $S'_2$ show possible alternative shapes for the surfaces $S_1$ and $S_2$, in the zones $ZS_1$ and $ZA_2$, respectively, which correspond to the same target-surface $S_0$. The new angle $A'_1$ is even larger than the angle $A_{10}$, and the surface $S'_1$ could even be produced with the tool 10 in a way that would be improved relative to a machining of the target-surface $S_0$.

The implementation of the invention in FIG. 3b relates to the placement of the machine tool 10 to produce the surface $S_1$ around a limit between two zones $ZA_1$ and $ZS_1$ that are adjacent, when the insert surface $S_1$ is again recessed in the zones $ZS_1$ relative to the zones $ZA_1$, and when the surface $S_1$ is continuous between the two zones $ZA_1$ and $ZS_1$ in question. At this zonal limit, the surface $S_1$ forms an angle $A_2$ between its portions that are in the separating zone $ZS_1$ and in the active zone $ZA_1$, respectively. This angle $A_2$ is obtuse, i.e. larger than 90°, whereas the angle $A_{20}$ of the target-surface $S_0$ is acute because of the sagittal height jump that is produced by the surface $S_2$ in this location. The positions indicated for the tool 10 show that the latter penetrates into the angle $A_2$ further than would have been possible for the angle $A_{20}$ of the target-surface $S_0$.

Lastly, the implementation in FIG. 3c relates to another configuration, in which the insert surfaces $S_1$ and $S_2$ are recessed in the active zones $ZA_1$, $ZA_2$, respectively, relative to the separating zones $ZS_1$, $ZS_2$, respectively. The angle $A_3$ is the re-entrant acute angle that is formed by the surface $S_2$ in the location of a sagittal height jump, between the direction of the jump and the portion of the surface $S_2$ that is located in the active zone $ZA_2$. This angle may be increased by removing an excess of material, designated by sup, from the insert 3 in the zone $ZA_2$, and by compensating this excess of material removed from the insert 3 by a surplus of material exc that is voluntarily left on the surface $S_1$ in the zone $ZS_1$. The thickness profile of the excess of material sup removed from the insert 3 may advantageously correspond to the profile of the tool 10, so that the latter can penetrate as far as the tip of the angle $A_3$. The thickness profile of the surplus of material exc that is left on the surface $S_1$ preferably corresponds to that of the excess of removed material sup, so that the resulting imaginary surface again coincides with the target-surface $S_0$. The angle $A_3$ of the surface $S_2$ that is thus modified becomes larger than the angle $A_{30}$ of the target-surface $S_0$.

By virtue of the improvement in the machining fidelity that is thus obtained for these three configurations, relative to the target-surface $S_0$, the lens 1 possesses an optical function that is closer to the target optical function. In particular, the lens 1 thus designed according to the invention produces less scattered light than the equivalent lens only a single face of which comprises adjacent Fresnel zones, without intermediate separating zones, for identical target-surfaces $S_0$. Typically, a factor-of-four width reduction, for strips in which the imaginary surface $S_F$ that is equivalent to the real lens 1 does not correspond to the target-surface $S_0$, changes the value from about 88% to a value of about 97%, for the contrast with which an image is formed through the lens.

Figure 4A:
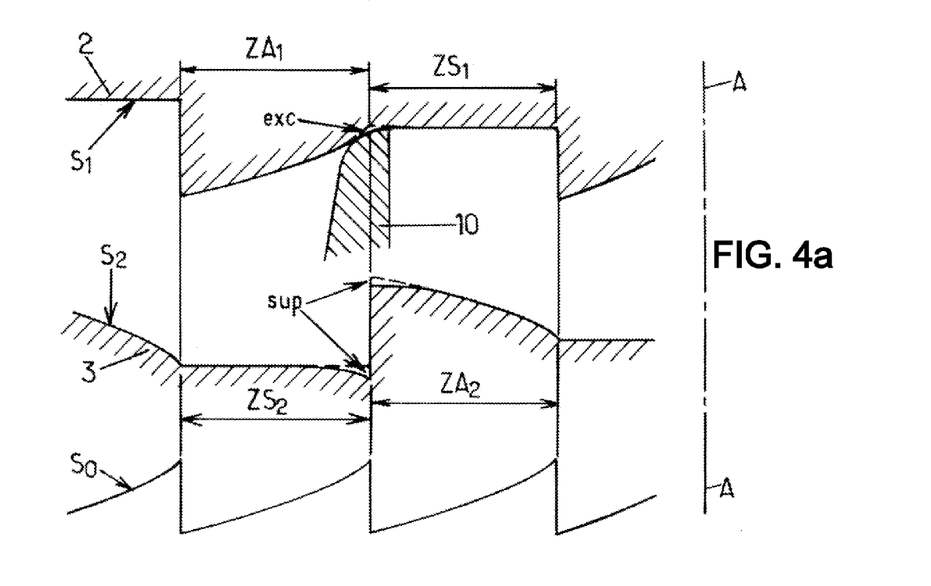
FIGS. 4a and 4b correspond to FIG. 3b, but using an improvement of the invention.

FIG. 4a illustrates an improvement in the invention, in the particular case of the configuration that has already been envisaged in FIG. 3b. Despite the increase in the angle $A_2$ that has been obtained by the invention, it is possible for the tool 10 to still not be able to form the extreme vertex of the angle $A_2$, especially when the tool 10 has a rounded back on the side opposite its angle of attack. In this case, machining leaves residual material on the surface $S_1$ of the insert 2, at the vertex of the angle $A_2$. This residue may then be compensated for by removing an excess of material from the surface $S_2$ of the insert 3, in line with the angle $A_2$. In fact, this improvement combines the effect of the invention just described for the angle $A_3$ (FIG. 3c), with the invention applied to the angle $A_2$. For this reason, the residual material that is left on the surface $S_1$ of the insert 2 is also indicated exc in FIG. 4a, and the excess of material that is removed from the surface $S_2$ of the insert 3 is indicated sup. The target-surface $S_0$ may thus be obtained with a greater exactitude at limits between active zones and separating zones to which this improvement is applied.

Figure 4B:
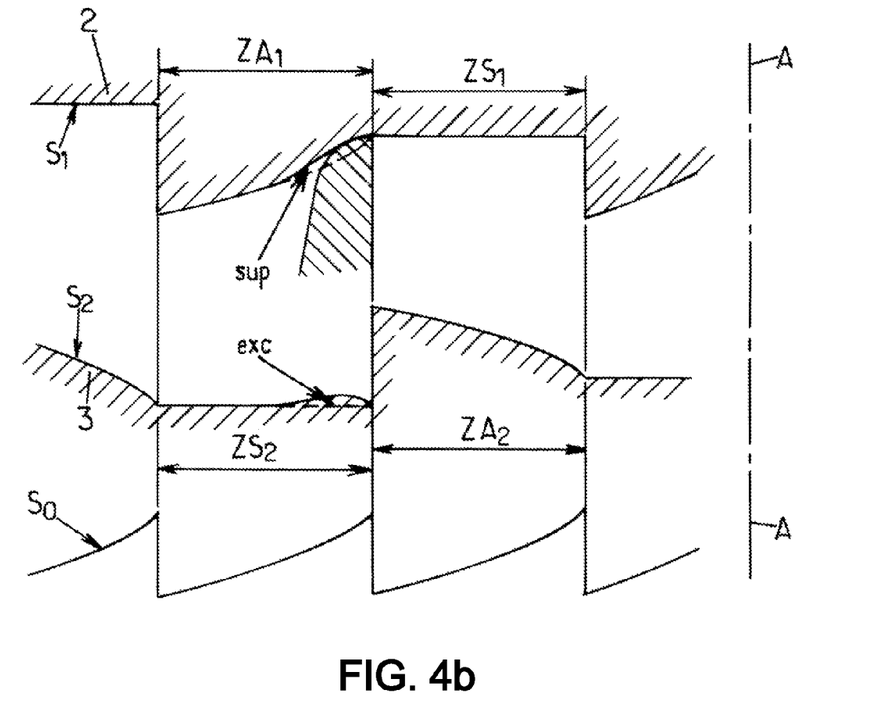
Figure 5A:
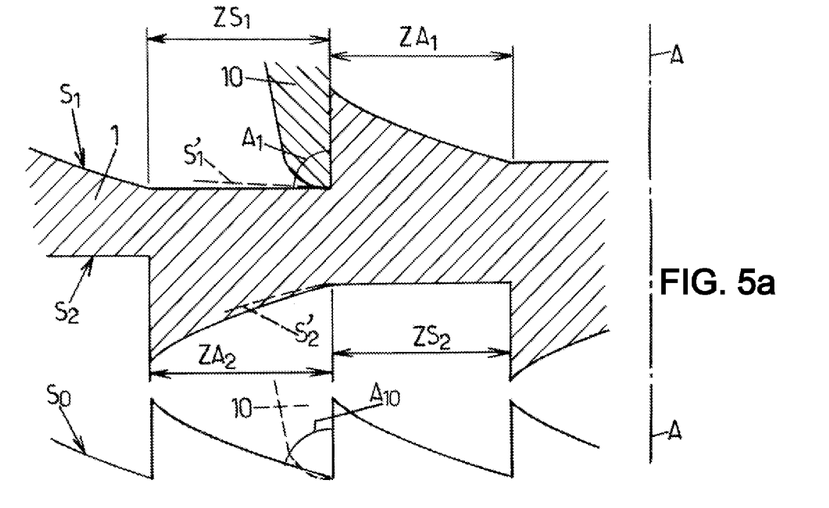
FIGS. 5a-5c and 6a-6b correspond to FIGS. 3a-3c and 4a-4b, respectively, for direct machining of the lens.
Figure 5B:
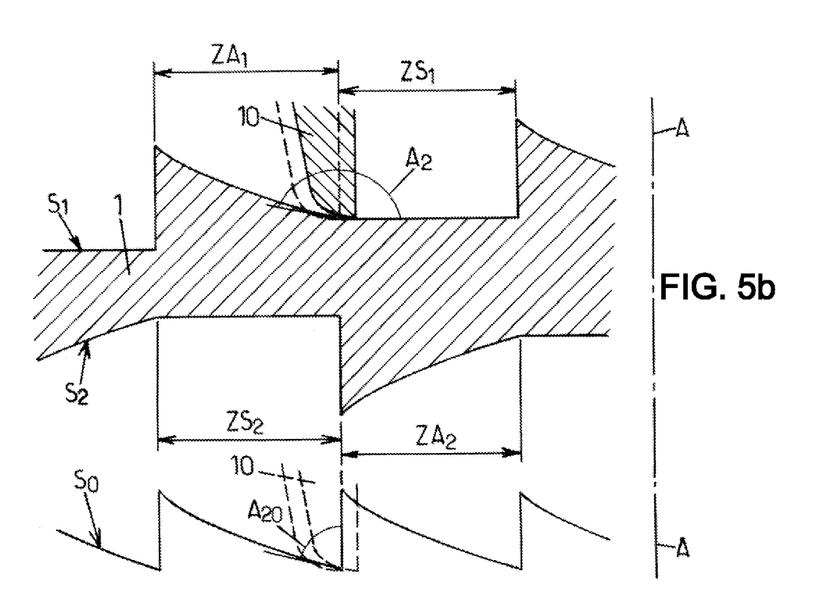
Figure 5C:
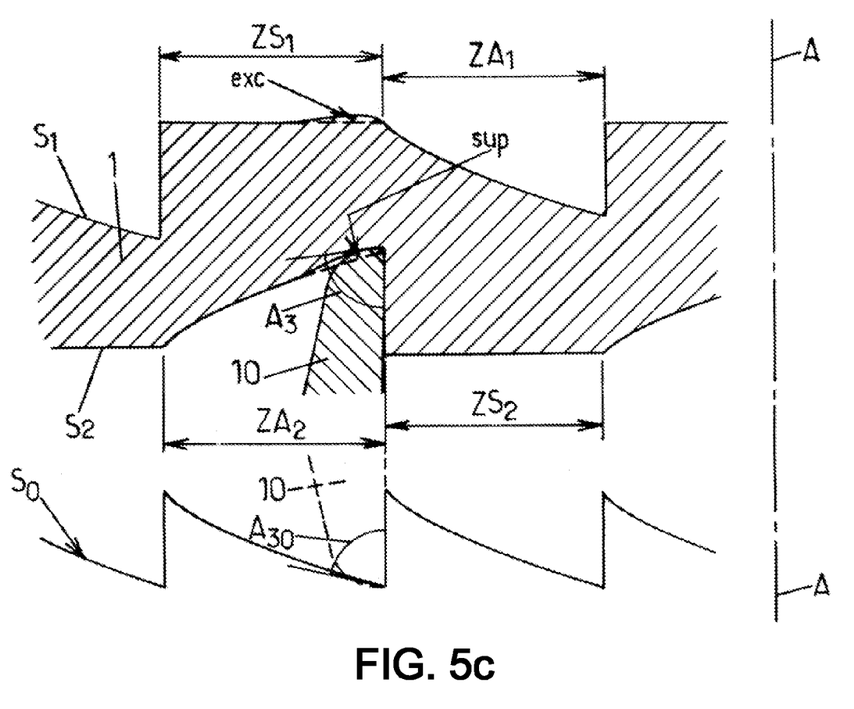
Figure 6A:
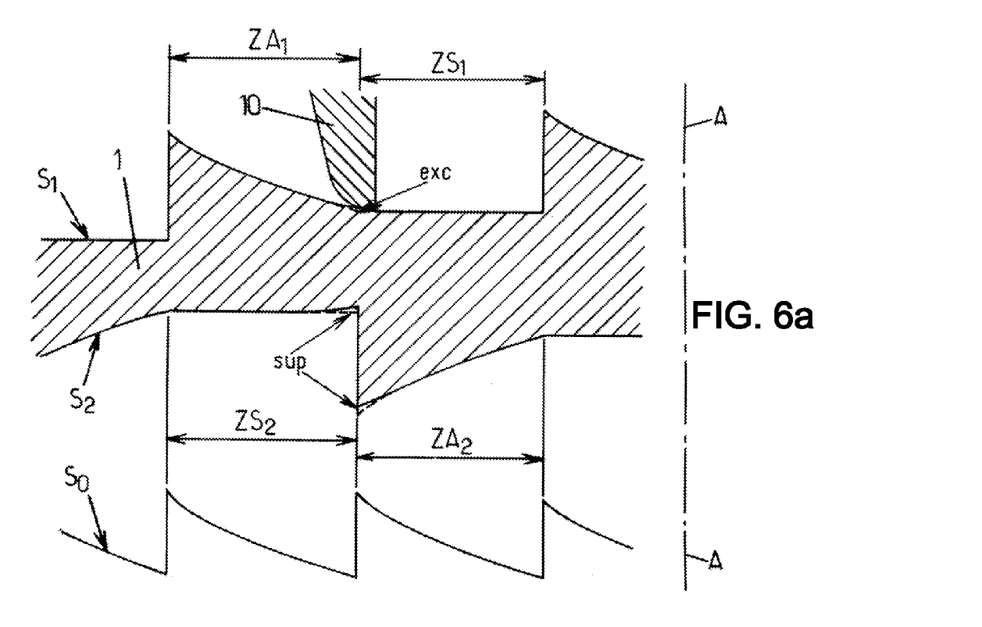
Figure 6B:
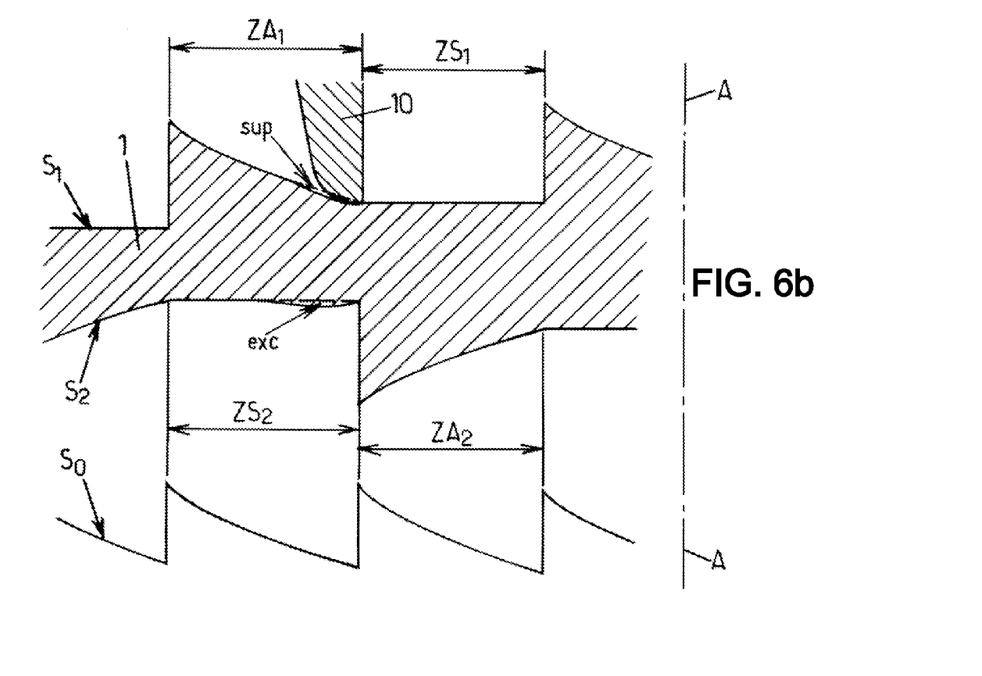

In FIG. 4a, the surface $S_1$ of the insert 2 has been machined so that the surplus of material exc is left on either side of the limit between the zones $ZA_1$ and $ZS_1$. FIG. 4b shows the case where the surface $S_1$ is produced with a trajectory of the angle of attack of the tool 10 that passes through the tip of the angle $A_2$. An excess of material sup is then removed from the insert 2, only in the active zone $ZA_1$. The surplus of material exc that is left on the surface $S_2$ of the insert 3 by way of compensation, is then limited to inside the separating zone $ZS_2$.

Moreover, each surface $S_1$ or $S_2$ may be produced by moving the tool 10 in a single direction, with its angle of attack being oriented toward the fore of the movement. This movement direction may be radial, centrifugal, or centripetal relative to the lens 1 when a lathe is used. The machining of each surface $S_1$, $S_2$ may thus be carried out in two passes of the tool 10, with each pass in a movement direction of the tool 10 that is opposite the movement direction of the other pass, and by reversing the tool 10 during an inversion of the pass direction.

Although the invention was described above for the case of the machining of molding inserts 2 and 3, this description may be transposed to the case of direct machining of the lens 1. FIGS. 5a-5c and 6a-6b illustrate the benefits that are provided by the invention for such direct machining. The angles that are considered are similar to those in FIGS. 3a-3c and 4a-4b, so much so that it is not necessary to repeat the explanations. The positions of the tool 10 are only reversed relative to the optical surfaces $S_1$ and $S_2$, because of the direct machining of the lens 1: the tool 10 is now outside the interval that is comprised between the surfaces $S_1$ and $S_2$.

Figures 7, 8:
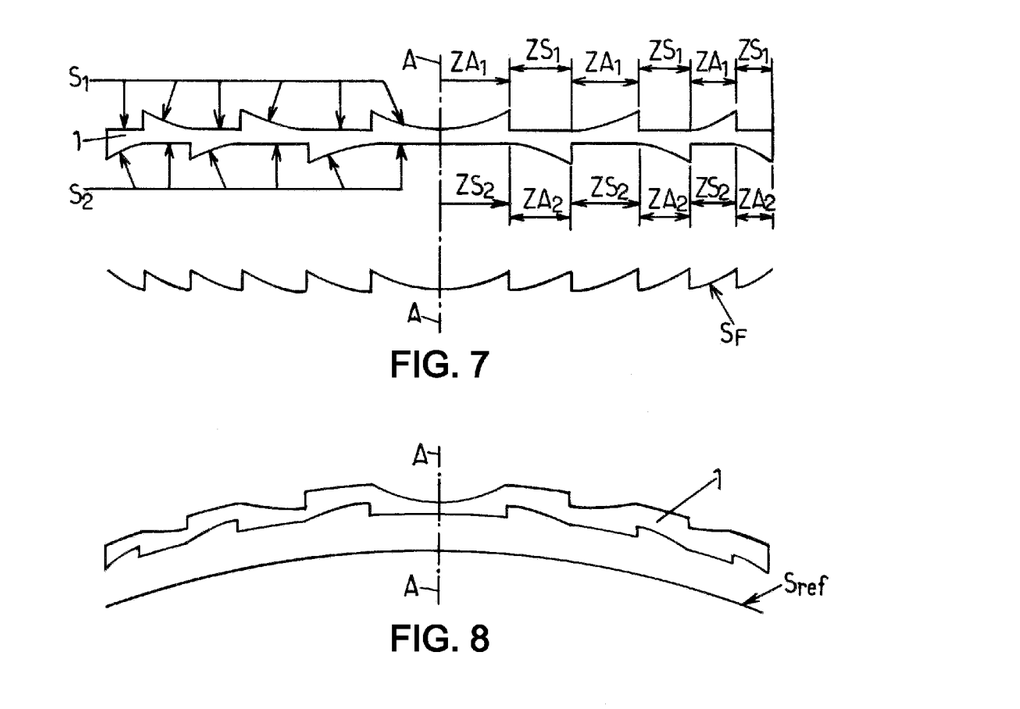
FIG. 7 corresponds to FIG. 2a for a variant of the invention.
FIG. 8 corresponds to FIG. 2a, for an ophthalmic lens intended to be assembled in a spectacle frame.

However, configurations are preferred, for the lens 1, in which one of the optical surfaces $S_1$ and $S_2$, or both, is (are) recessed in at least one of the separating zones $ZS_1$ or $ZS_2$, respectively, relative to this (these) same surface(s) in the active zones $ZA_1$ or $ZA_2$, respectively, which are adjacent to the separating zone in question. The weight of the lens 1 may then be decreased, for an optical function of the lens that is identical. Even more preferably, each of the optical surfaces $S_1$ and $S_2$ of the lens 1 may be recessed in each separating zone relative to the same surface in the active zones that are adjacent to the separating zone in question. FIG. 7 corresponds to FIG. 2a for such a configuration of the optical surfaces of the lens.

It will be understood that the invention, which has been described in detail for a divergent Fresnel lens, may be applied in the same way to a convergent Fresnel lens.

It will also be understood that the invention may be applied in the same way to an ophthalmic lens, as shown in FIG. 8. To do this, a non-zero reference curvature value, called the base curvature, is added to the two optical surfaces $S_1$ and $S_2$. Such a base value may especially be incorporated into the reference surface that is used to measure the sagittal heights of the two optical surfaces. The reference surface is then widely called the "base" in the terminology used by those skilled in the art. In FIG. 8, $S_{ref}$ designates such a base, or reference surface, having a non-zero curvature.

Figure 9A:
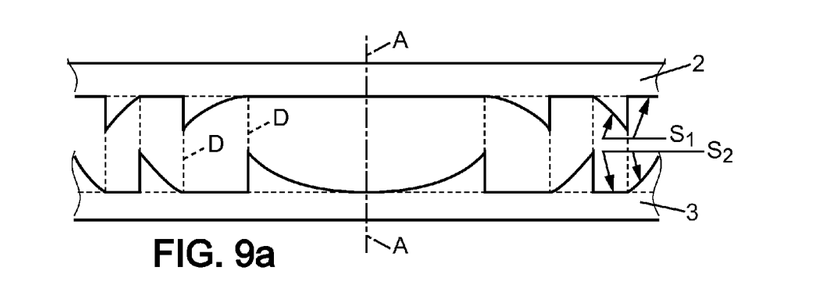
FIGS. 9a to 9d correspond to FIG. 2b for a number of variant sagittal height jump directions.
Figure 9B:
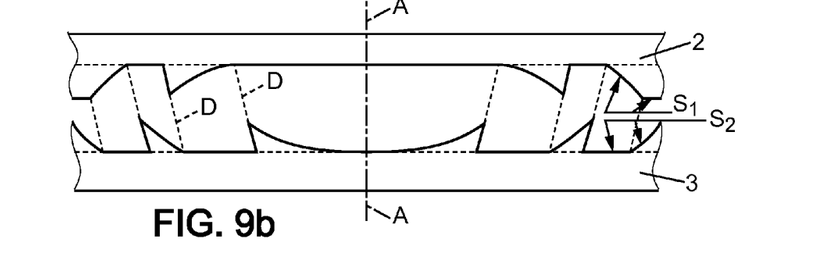
Figure 9C:
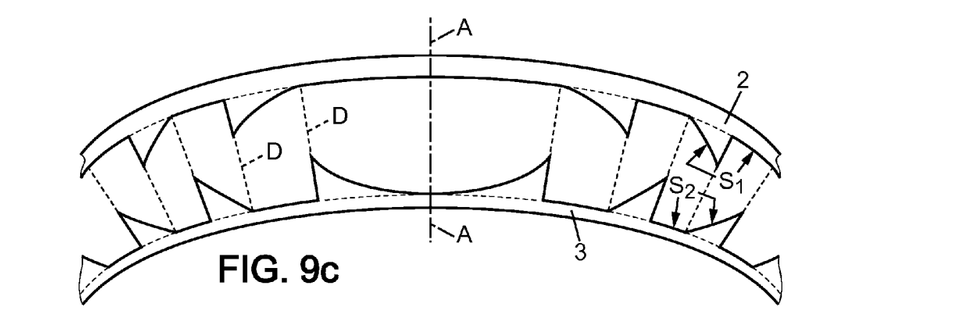
Figure 9D:
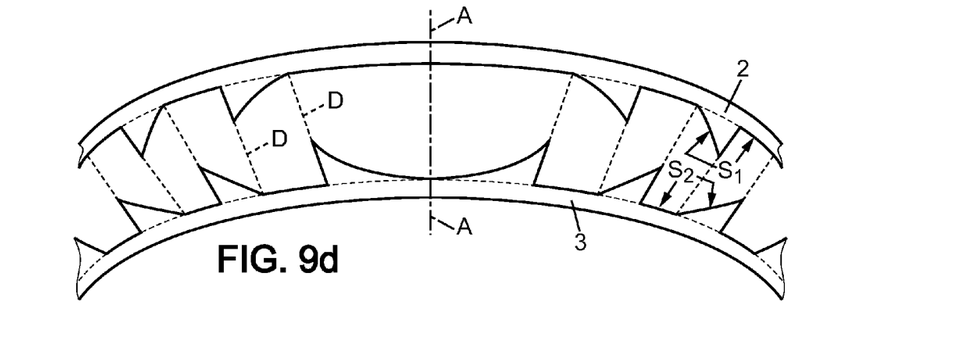

FIGS. 9a and 9b illustrate embodiments of the invention when the reference curvature is zero, in other words when the base of the lens is planar, and FIGS. 9c and 9d other embodiments of the invention when the base is cambered. In the embodiments in FIGS. 9a and 9c, the directions D of alignment of the height jumps that are located facing, on the surfaces $S_1$ and $S_2$, respectively, are perpendicular to the base, which is shown in dotted lines for each surface. Because the base is planar in FIG. 9a, the direction D is parallel to the optical axis A-A of the lens. Furthermore, the direction D is the direction of each height jump, i.e. the discontinuity direction of each of the surfaces $S_1$ and $S_2$. However, generally, the direction of the height jumps may be inclined relative to the direction that is perpendicular to the base in the location of the height jump. Such a possibility is shown in FIG. 9b for the planar base, and in FIG. 9d for a cambered base. In both cases, the direction of the height jumps is again coincident with the direction D of alignment of the zonal limits that are located facing. Such a configuration is preferred because it decreases the visibility of the zonal structures of the lens, and the discomfort that could result therefrom for a user of the latter.

It will also be understood that the invention may be applied to lenses each having more than two optical surfaces, for example three or four optical surfaces, which the light rays pass through in succession. In this case, the active zones and the separating zones of all these optical surfaces may be combined in various ways, while applying the features of the invention. From the description that was given above of the present invention, those skilled in the art will be able to apply the invention without difficulty to such more complicated lenses. In addition, the optical surfaces to which the invention is applied may be exposed to the ambient environment, or be covered with a transparent layer, for example a layer of resin. Such a layer, which has a luminous refractive index value different from that of the polymer of the lens, may especially protect the sagittal height jump structure from scratches or the deposition of dirt.

It is also possible to form a lens according to the invention, by producing separately a plurality of lens parts that are then assembled with one another to form the complete lens. In this case, the optical surfaces to which the invention is applied may be borne by the various parts of the lens. Their assembly is then carried out so as to align the limits between active zones and separating zones of initially separate parts, along the optical axis of the lens, in order to obtain the advantages of the invention. Such an assembly may be carried out by adhesively bonding parts to one another, for example using an adhesive that is limited to a peripheral contour of the lens.

Figure 10:
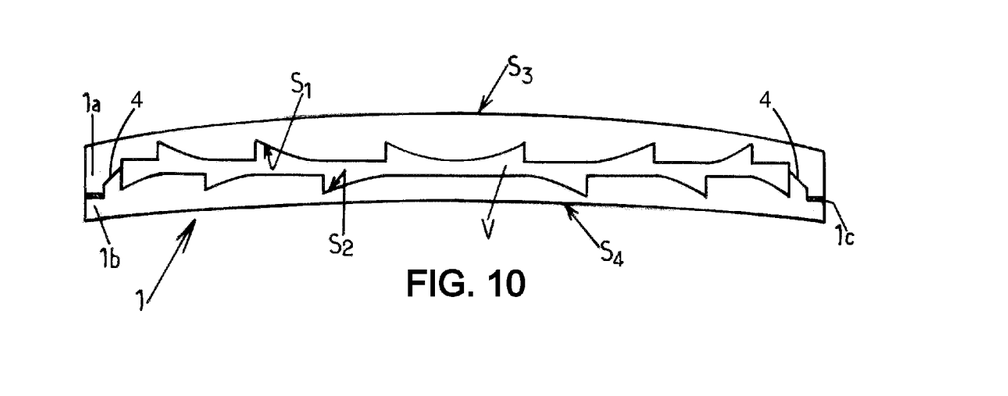
FIG. 10 is a cross section of another lens according to the invention.

FIG. 10 is a cross-sectional view of such a lens 1 that is in accordance with the invention, it being made up of two lens parts 1a and 1b designed so that the zoned optical surfaces $S_1$ and $S_2$ are turned towards the interior of the lens. The reference 1c indicates the peripheral adhesive bonding zone where the parts 1a and 1b are bonded together. The reference 4 designates relief patterns that are borne by the two lens parts 1a and 1b outside of their respective optical surfaces $S_1$ and $S_2$, for example around these surfaces. These patterns 4 are complementary from one lens part to the other, so that interfitting them guarantees the alignment of the optical surfaces $S_1$ and $S_2$, this alignment being provided for by the invention. Optionally, the space V that is enclosed between the surfaces $S_1$ and $S_2$ may be suitably filled in order to provide the lens 1 with an additional function. The exterior optical surfaces of the lens 1 that is thus formed, referenced $S_3$ and $S_4$, may furthermore be machined in order to provide additional contributions to the total optical power of the lens. Such machining of one or both surfaces $S_3$ and $S_4$ is preferably carried out after definitive assembly of the two lens parts 1a and 1b.

The invention claimed is:

1. A lens (1) comprising at least two optical surfaces ($S_1$, $S_2$) each extending transversely relative to an optical axis (A-A) of the lens, so that light rays that pass through the lens pass through one then the other of the two surfaces, each surface comprising active zones ($ZA_1$, $ZA_2$) inside of which a shape of said surface is adapted to produce part at least of the optical power of the lens for rays that pass through said active zones, with a sagittal height discontinuity of each surface between two different active zones of said surface, limits of the active zones ($ZA_1$, $ZA_2$) of a first of the two surfaces being located in line with limits of the active zones of the other of said two surfaces, the lens being characterised in that said first and second surfaces ($S_1$, $S_2$) furthermore comprise separating zones ($ZS_1$, $ZS_2$) arranged so that each of the first and second surfaces consists of an alternation between the active zones and the separating zones, each active zone ($ZA_1$, $ZA_2$) of one of the first and second surfaces ($S_1$, $S_2$) being in line with a separating zone ($ZS_2$, $ZS_1$) of the other of said first and second surfaces, and the shape of at least one of the first and second surfaces ($S_1$, $S_2$) in at least one of the separating zones ($ZS_1$, $ZS_2$) is adapted to increase at least one of the following angles:

a first angle ($A_1$) formed by said surface ($S_1$, $S_2$) in said separating zone ($ZS_1$, $ZS_2$) with a direction of a sagittal height jump located at a limit between said separating zone and an active zone ($ZA_1$, $ZA_2$) adjacent to said separating zone, a second angle ($A_2$) formed by said surface ($S_1$, $S_2$) at a limit of between said separating zone ($ZS_1$, $ZS_2$) and an active zone ($ZA_1$, $ZA_2$) adjacent to said separating zone, and a third angle ($A_3$) formed by the other surface ($S_2$, $S_1$) at a limit of the active zone ($ZA_2$, $ZA_1$) of said other surface that is located in line with said separating zone ($ZS_1$, $ZS_2$), said third angle being formed by said other surface in said active zone with a direction of a sagittal height jump located at the limit of said active zone, relative to an angle ($A_{10}$, $A_{20}$, $A_{30}$) located at a given location of the lens (1) and formed by an imaginary surface ($S_0$) obtained by subtracting respective sagittal heights of the first and second surfaces ($S_1$, $S_2$), said angle for the imaginary surface being acute.

2. The lens as claimed in claim 1, in which, for at least one of the first and second surfaces ($S_1$, $S_2$), said surface has a shape, on at least one side of a sagittal height jump of said surface, at the limit between a separating zone ($ZS_1$, $ZS_2$) and an active zone ($ZA_1$, $ZA_2$), adapted to compensate a forming defect at the tip of an angle ($A_2$) of the other surface located in line with said limit.

3. The lens as claimed in claim 1, in which the active zones ($ZA_1$, $ZA_2$) and the separating zones ($ZS_1$, $ZS_2$) are concentric inside each of the first and second surfaces ($S_1$, $S_2$).

4. The lens as claimed in claim 1, in which, for at least one of the limits between an adjacent active zone ($ZA_2$, $ZA_2$) and separating zone ($ZS_1$, $ZS_2$) of one of the optical surfaces ($S_1$, $S_2$), a sagittal height jump direction at said limit is coincident with a direction (D) of alignment of said limit with a limit between adjacent separating and active zones of the other optical surface.

5. The lens as claimed in claim 1, for which the part of the optical power of said lens that is produced by the first and second surfaces ($S_1$, $S_2$) results from a refraction or a diffraction of light in the active zones ($ZA_2$, $ZA_2$) and the separating zones ($ZA_2$, $ZA_2$) of each surface.

6. The lens as claimed in claim 1, of the ophthalmic lens type, including therein spectacle glasses, contact lenses and ocular implants.

7. The lens as claimed in claim 1 in which, for at least one of the first and second surfaces ($S_1$, $S_2$), said surface in at least one of the separating zones ($ZS_1$, $ZS_2$) is recessed relative to said surface in the active zones ($ZA_1$, $ZA_2$) adjacent to said separating zone.

8. The lens as claimed in claim 7 in which, for each of the first and second surfaces ($S_1$, $S_2$), said surface in each separating zone ($ZS_1$, $ZS_2$) is recessed relative to said surface in the active zones ($ZA_1$, $ZA_2$) adjacent to said separating zone.

9. The lens as claimed in claim 1, in which a sagittal height variation amplitude of each of the first and second surfaces ($S_1$, $S_2$) in at least one of the separating zones ($ZS_1$, $ZS_2$) of said surface is smaller than 25% of a sagittal height variation amplitude of the other surface in the active zone ($ZA_1$, $ZA_2$) located in line with said separating zone.

10. The lens as claimed in claim 9, in which each of the first and second surfaces ($S_1$, $S_2$) is planar or corresponds to a cambered base of said lens inside each separating zone ($ZS_1$, $ZS_2$).

11. The lens as claimed in claim 1, comprising at least two separate lens parts (1a, 1b), a first of said lens parts forming the first optical surface ($S_1$), and a second of said lens parts forming the second optical surface ($S_2$), and the first and second lens parts being arranged so that said first and second optical surfaces are turned toward each other.

12. The lens as claimed in claim 11, in which the first and second lens parts (1a, 1b) have complementary patterns (4) in a peripheral zone of the lens, said patterns being adapted to produce an alignment of said first and second lens parts relative to each other during assembly of said lens parts to form the lens.

13. An assembly for forming a lens, comprising two master-surfaces adapted to form the first and second optical surfaces ($S_1$, $S_2$), respectively, of a lens (1) as claimed in claim 1.

14. The forming assembly as claimed in claim 13, consisting of a pair of embossing matrices or a pair of molding inserts (2, 3), said embossing matrices or molding inserts comprising the first and second master-surface, respectively.

* * * * *